United States Patent
Hyvarinen et al.

(10) Patent No.: US 7,469,031 B2
(45) Date of Patent: Dec. 23, 2008

(54) MAMMOGRAPHY IMAGING APPARATUS

(75) Inventors: Pentti Hyvarinen, Helsinki (FI); Sami Tohka, Porvoo (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 10/595,906

(22) PCT Filed: Nov. 29, 2004

(86) PCT No.: PCT/FI2004/000727

§ 371 (c)(1),
(2), (4) Date: Apr. 9, 2007

(87) PCT Pub. No.: WO2005/051199

PCT Pub. Date: Jun. 9, 2005

(65) Prior Publication Data

US 2007/0274438 A1    Nov. 29, 2007

(30) Foreign Application Priority Data

Nov. 28, 2003 (FI) .................................. 20031750

(51) Int. Cl.
*A61B 6/04* (2006.01)
*H05G 1/02* (2006.01)

(52) U.S. Cl. .......................... 378/37; 378/195

(58) Field of Classification Search ............ 378/37, 378/195–197, 205
See application file for complete search history.

(56) References Cited

U.S. PATENT DOCUMENTS

| 5,018,176 | A | 5/1991 | Romeas et al. |
| 5,305,365 | A | 4/1994 | Coe |
| 6,292,531 | B1 | 9/2001 | Hsieh |
| 6,611,575 | B1 | 8/2003 | Alyassin et al. |
| 6,999,554 | B2 * | 2/2006 | Mertelmeier ............... 378/37 |
| 2003/0198315 | A1 * | 10/2003 | Andreasson et al. .......... 378/37 |
| 2005/0100129 | A1 * | 5/2005 | McKenna .................... 378/37 |

FOREIGN PATENT DOCUMENTS

FI    944764    4/1996

\* cited by examiner

*Primary Examiner*—Irakli Kiknadze
(74) *Attorney, Agent, or Firm*—WolfBlock LLP

(57) ABSTRACT

Mammography imaging apparatus according to the invention contains e.g. an essentially vertically standing body part and an arm structure in connection with it, being turnable with respect to a horizontal rotating axis, a radiation source on one hand and image data receiving means on the other hand being located at essentially opposite ends of the arm structure. The arm structure includes at least two arm parts orientating essentially parallel and means for changing mutual orientation of at least the first and the second of the said at least two arm parts, first means for turning the said first arm part around a horizontal axis and second means arranged to the said second arm part with help of which, when turning the said first arm part, it is possible both to maintain orientation of the said second arm part with respect to the said first arm part and to turn the said second arm part in a different direction and/or at a different angular velocity with respect to the movement of the said first arm part.

23 Claims, 4 Drawing Sheets

MAMMOGRAPHY IMAGING APPARATUS

Figure 1:
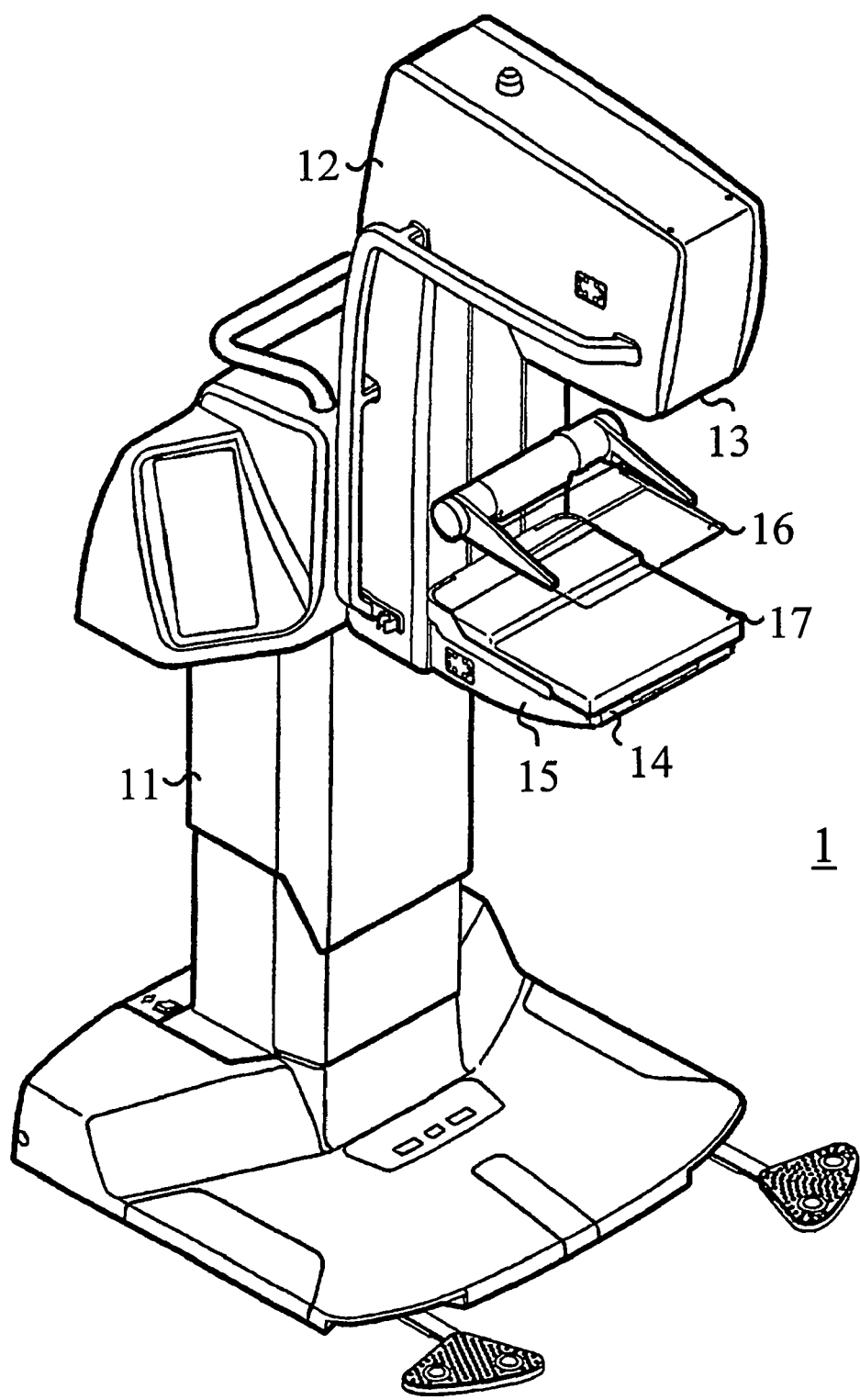

The present invention relates to a structure of a mammography imaging apparatus, especially to a turnable arm structure of a mammography imaging apparatus including an x-ray tube and image data receiving means, and to a method and a control arrangement for turning such an arm structure.

More precisely, the object of the invention is a mammography imaging apparatus according to the preamble of claim 1, its control arrangement and a method according to the preamble of claim 13 for turning the arm structure of a mammography imaging apparatus. Thus, the object of the invention contains either an essentially vertically standing body part or a support structure attachable to a wall or a ceiling and an arm structure in connection with it, being turnable with respect to a horizontal pivot axis, a radiation source on one hand and image data receiving means on the other hand being placed at essentially opposite ends of the arm structure, which arm structure includes at least two arm parts orientating essentially parallel and means for changing the mutual orientation of at least two of the said at least two arm parts. Typically a mammography imaging apparatus contains also a compression paddle structure in connection with the arm structure for positioning and keeping the tissue to be imaged at its place within the imaging area, and often also a possibility for connecting various accessories, such as biopsy equipment to the imaging apparatus. Image data receiving means are often arranged to be replaceable to meet requirements of various imaging modes.

In mammography it is extremely important to avoid unnecessary exposure of the tissue to be imaged to the x-ray beams, i.e. radiation hygiene. Unnecessary exposure can be avoided especially by attempting to ensure success of the imaging, whereupon there won't be need for subsequent retakes due to unsuccessful imaging itself at least. One potential reason for unsuccessful imaging is a faulty or inaccurate positioning of the tissue to be imaged into the imaging area before imaging. If e.g. the tissue closest to thorax, which is just the area where a tumor is often located, will not become imaged, a consequence may be a false diagnosis even—based on the images taken—in the subsequent diagnosis phase.

On the other hand, time spent on imaging is pertinent in screening imaging being directed to crowds of patients. E.g. uncomfortable working postures in connection with patient positioning may cause not only ergonomic problems to the personnel assisting the imaging, but they may easily lead to unnecessary waste of time in the preliminary preparations for the imagings as well. Naturally, also the time always required for being able to drive the moving parts of the imaging apparatus to their next desired emplacement has direct influence on the overall time spent on the imaging.

A typical mammography apparatus contains a rotatable arm structure, which is traditionally implemented as a fixed solid part, as a so-called C-arm, a radiation source on one hand and image data receiving means on the other hand being placed in parts of the arm diverging from the essentially opposite ends of a longitudinal body part of it. Due to various reasons relating to construction and imaging technique, the structure and dimensions of a mammography apparatus are typically such that when positioning the patient to be imaged, and the C-arm being in vertical position, the relatively large x-ray tube structure is situated approximately in the same neighborhood as the head of the patient. Positioning of tissue into the imaging area may then be awkward as the tube head impedes optimal emplacing of the patient with respect to the imaging apparatus, and possibly also work of the person assisting the emplacing. The latter problem will be readily emphasized even when the C-arm is turned into an oblique view position, because then either a large tube head, and correspondingly on the other side the parts of the C-arm structure underneath it, will place themselves exactly within the space where it would be most natural for the person assisting with the positioning of tissue to stand and work. Thus, the assisting person may end up reaching over structures of the imaging apparatus, stooping underneath them or otherwise into unergonomic and uncomfortable working postures.

Consequently, prior art includes solutions that enable moving the x-ray tube head away from its imaging position for the duration of patient positioning. These kind of structures are described e.g. in FI patent application 944764, according to which it is possible to arrange to the C-arm various possibilities to move aside an "upper branch" of the C-arm including the tube head itself, or to turn it backwards from its imaging position. As an actual invention in that publication is presented relocation of the tube head out of the way automatically, and expressly in connection with oblique view imaging, but it is also presented that the solution will make it easier to fit to the x-ray apparatus accessories, which are to be used in biopsy performed in connection with mammography inspections.

Problems concerning expressly biopsy are described also in the U.S. Pat. No. 5,018,176, which teaches such a modified C-arm of a mammography apparatus that consists of two longitudinal arm parts, the arms being arranged rotatable as connected to each other around the same horizontal rotating axle by one actuator but in such a way, however, that the connection between the arm parts is detachable. Thereby in a structure according to the publication, depending on the connection status, the (lower) arm part containing a film cassette either rotates or doesn't rotate together with the (upper) arm part containing a radiation source. It is presented that with help of the structure, use of that apparatus in stereo imaging in connection with biopsy operation is facilitated, which imaging is realized according to the publication by positioning an object at the level of the rotating axel of the arm structure of the imaging apparatus, located at a distance from the image data receiving means, and by taking two images of the object from different projections.

The object of the present invention is to bring about improvements to the problems presented above and to the apparatus constructions known from the publications mentioned above. Especially an objective of the invention is to create a mammography apparatus, which offers a novel way of arranging a clearer working area for positioning tissue into the imaging area before actual imaging, whereby emplacement of the patient and positioning of the object to be imaged into the imaging area become easier.

Essentially one talks about then particularly an object to be able to move a radiation source, being connected with a swivel arm structure of a mammography apparatus, out of the space hampering the positioning (and/or, correspondingly, to move a bottom part of an arm structure possibly hampering positioning), especially e.g. in connection with the so-called contact imaging used in context of common screening imaging, in which imaging the means for receiving image data are located in a so-called lower shelf structure diverging essentially from the bottom end of the arm structure, and in which the tissue to be imaged is positioned motionless with help of a compression paddle structure of the imaging apparatus within an imaging area located in the vicinity of the image data receiving means—i.e. in practise in such a way that the tissue to be imaged is in direct contact with the structures located immediately above the means for receiving image data. Depending on the apparatus, this contact surface may be e.g. a separate compression paddle drivable onto the lower shelf structure or a fixed upper surface of that lower shelf structure, which upper surface then serves, in fact, also as a lower compression paddle. Between such a surface and image data receiving means there has typically been arranged a grid structure, a so-called bucky, which prevents the radiation quanta scattered off the tissue from becoming imaged. In such imaging the invention especially concerns, typically, the distance between the object positioned to be imaged and the image data receiving means is in the order of magnitude of millimeters.

One object of the invention is to realize a mammography apparatus according to abovementioned objects without complicated new structural arrangements. E.g. an arrangement taught by prior art according to the FI application 944764 to facilitate positioning is based on arranging totally new types of degrees of freedom of movement for the x-ray tube, whereby need for a completely new structure of the C-arm arises for making such movements possible.

Further object is to enable implementing the invention in such a way that movements of the arm structure may be easily realized programmatically. The object is to implement a mammography apparatus by using an arm structure which includes at least a first and a second arm part, of which the first one contains a radiation source and the second one means for receiving image data, and the orientation of those arm parts in a vertical plane being arranged to be changeable with respect to each other.

Further, an object of the invention is to implement a rotating arm structure of a mammography apparatus in such a way that driving of the arm parts into various desired positions is flexible and effective.

An object of the invention is also to achieve a method and a control arrangement enabling its implementation, with help of which such turning sequences may be realized by an arm structure of a mammography apparatus by which the arm structure may be flexibly driven into various imaging positions in stages, thanks to which stages easier positioning of the object to be imaged into the imaging area is made possible.

Essential features of the invention are presented in the following independent patent claims. The invention is based on the insight that the C-arm structure traditionally used in mammography apparatuses can be realized as such a structure consisting of at least first and second arm parts, which structure includes first means for turning at least the said first arm part around a horizontal axis and in which to the said second arm part has been arranged second means, with help of which—while the said first arm part is being turned—orientation of the said second arm part with respect to the said first arm part may be both maintained and the said second arm part may be turned into a different direction and/or at a different angular velocity with respect to the movement of the said first arm part.

Especially the invention denotes a construction where the said first means comprise a construction containing an actuator, which construction is arranged to turn the arm structure as a whole with respect to a horizontal axis both clockwise and counter clockwise, and the said second means preferably a construction comprising a second actuator, with which construction orientation of one of the arm parts with respect to at least one other arm part may be changed. However, the said second means may also contain e.g. such a gear arrangement through which, when turning the said first arm part, the said second arm part either follows movement of the said first arm part or turns at a different angular velocity and/or in another direction than the said first arm part. Although the actuators for turning the first and the second arm part could be considered to be arranged as independent, it is in many ways advantageous to implement the invention expressly in such a way that one actuator turns the whole arm structure as an entity and the said second means then take care of orientation of at least one of the arm parts with respect to at least one other arm part. This enables e.g. modification of existing constructions to be in accordance with the invention by relatively small structural alterations, as the construction already in existence for turning the arm structure as a whole may be utilized. This kind of a solution is also in many ways simpler than turning the arm parts completely independently, especially since the actual goal of the invention does not require substantial deviation, e.g. 90 or even 180 degrees, of mutual orientation of the arm parts from parallel.

Figure 2:
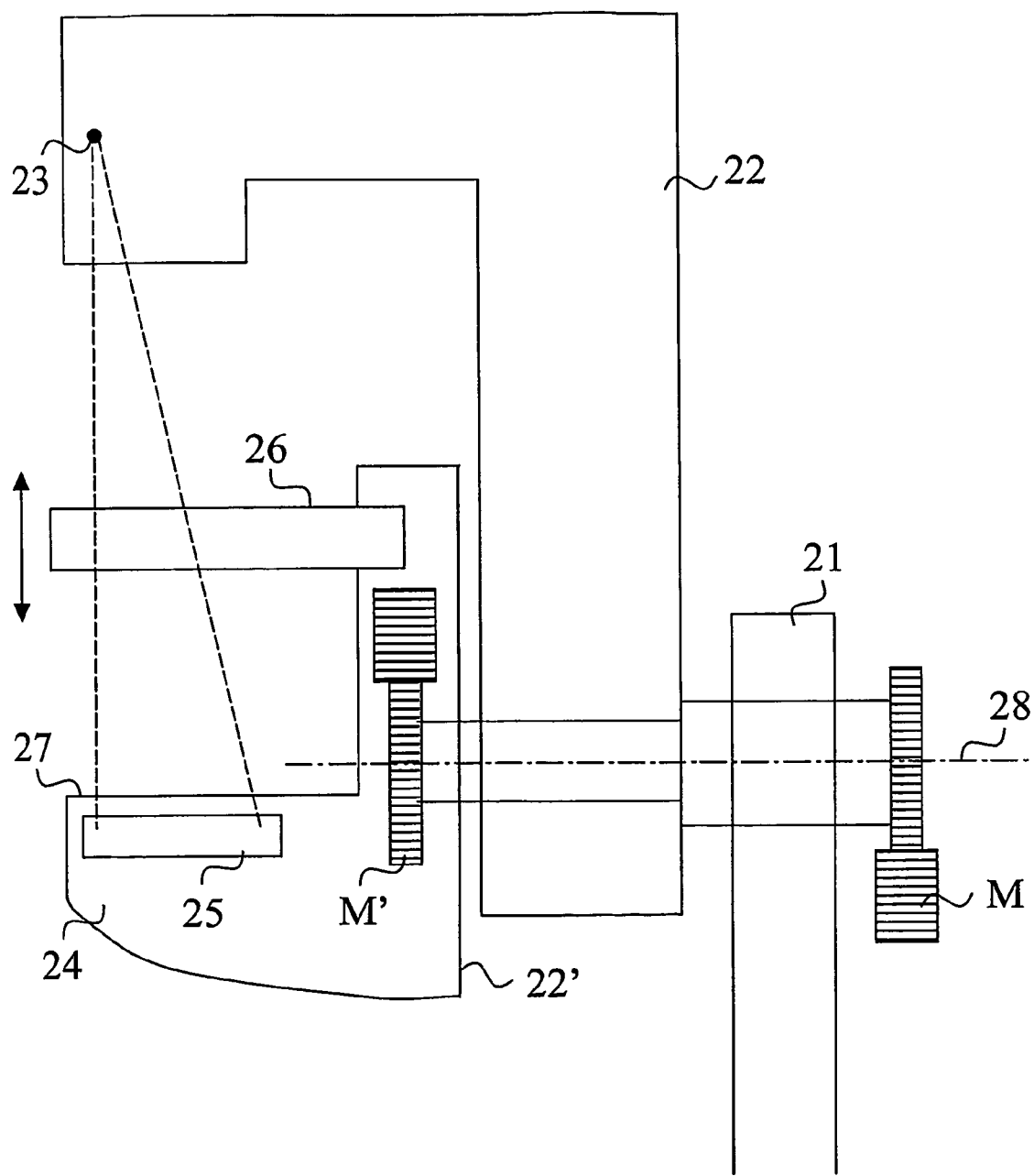

Some embodiments of the invention and benefits of them will be described more precisely in the following, also with help of the attached figures, of which figures FIG. 1 presents a mammography apparatus including a traditional C-arm structure FIG. 2 presents a structure of a mammography apparatus according to a preferable embodiment of the invention as a side view FIGS. 3a-3d present one sequence-of-use of an arm structure according to the invention.

A mammography apparatus 1 presented in FIG. 1 consists of a body part 11 and a C-arm 12 in connection with it. Typically, at the opposite ends of the C-arm 12 are situated a radiation source 13 and, e.g. inside a so-called lower shelf structure 14, image data receiving means 15, which depicting means 13, when being located inside the cover of the apparatus are actually not visible in FIG. 1. Additionally, within the area between these depicting means 13, 15, typically at the proximity of the image data receiving means 15, there has been placed means 16, 17 for positioning the object to be imaged within the imaging area. Typically, the C-arm 12 is movable both in vertical direction with respect to the means 16, 17 for positioning the object to be imaged and rotatable with respect to the body part 11. The positioning means 16, 17 typically consist of an upper compression paddle 16 and a lower compression paddle 17, which lower compression paddle 17 may be arranged to function even as a so-called bucky, too. "Bucky" means a grid structure located between the tissue to be imaged and the image data receiving means, which grid structure limits entry of radiation scattered from the tissue to the image data receiving means.

A structure of a mammography apparatus according to the invention presented in FIG. 2 contains a first arm part 22 and a second arm part 22', of which essentially at the end of the first arm part 22 there has been placed a radiation source 23 and, correspondingly, at the end of the second means for receiving image data 25. In the structure according to FIG. 2, the upper compression paddle 26 is arranged to be linearly movable with respect to the second arm part 22', and the lower compression paddle 27 for its part in a fixed position with respect to the second arm part 22'—possibly as an integrated part of a lower shelf structure 24 belonging to it. The upper surface of the lower compression paddle 27 resp. the lower shelf structure 24 is typically essentially planar, the said plane being essentially parallel with the rotating axle 28. The lower compression paddle 27 is preferably arranged in a position that is essentially at the immediate proximity of and below the rotating axle 28, the axle 28 being arranged to be common for the first and the second arm parts 22, 22'—when the said second arm part 22' is in a vertical position. Thereby, the middle axis of a breast that is compressed in an imaging position essentially coincides with the said rotating axle 28, which is preferable in view of patient positioning in many of the applications of the apparatus according to the invention, e.g. when moving from one imaging projection angle to another.

Correspondingly to that of the upper compression paddle 26, the lower compression paddle 27 may also be arranged linearly movable, but according to a preferable embodiment of the invention, even then it may also be emplaced in a position that is located in a corresponding way with respect to the rotating axle 28 of the arm parts as previously described, and in that case preferably, too, correspondingly as described above, with respect to the image data receiving means 25. As far as dimensions of the structure in practise are concerned, a structure is considered in which distance between the focus of the radiation source 23 and the image data receiving means 25, which include to the said first and the second arm parts 22, 22', respectively, is in the order of magnitude of 60-80 cm when the said arms 22, 22' are orientated essentially parallel, and the distance from the surface of the lower compression paddle 27 to the rotating axle 28 then centimeters, like 1-5 cm, preferably ca. 2-3 cm. FIG. 2 is not drawn in scale but only for demonstrating a structure according to the invention whereby, e.g. when distance from the surface of the lower compression paddle 27 to the image data receiving means 25 is in a construction according to FIG. 2 in practise in the order of magnitude of millimeters, the previously mentioned distance, inter alia, between the rotating axle 28 and the surface of the lower compression paddle 27, for instance, corresponds in practise also to the distance between the rotating axle 28 and the image data receiving means 25. The image data receiving means 25 may be any such means of prior art, like a film cassette or a digital detector.

In the preferable embodiment of the invention presented in FIG. 2 there has been arranged actuators M, M' for both of the arm parts for turning them around a pivot axle 28 common to the arm parts. The structure is preferably implemented in such a way that the first of the actuators M turns the arm structure as a whole and the second only the second arm part 22', but in principle the construction may also be implemented in such a way that the second arm part 22' does not move along with the movement of the first arm part 22 but only as moved by its own actuator M'. Without going into any structural details obvious to a man skilled in the art, a construction according to the invention may be implemented preferably in such a way that, when one desires to turn both of the arms at the same angular velocity in same direction the actuator M turning the whole arm structure will be used, but when one desires to drive the arms in opposite directions and/or at different angular velocities, both of them will be used. It is preferable to arrange the actuator turning only one arm part in direct connection with that arm part in question, whereby construction of the apparatus may be implemented in a way preferable from the point of view of the invention as specifically described in the previous paragraph, whereby both the benefits brought about by the essential coinciding of the pivot axle 28 to the middle axis of the object to be imaged and those given by the opportunities of movements of the arm parts according to the invention, are utilizable in an optimal way, expressly in the context of contact imaging used in the screening imaging. In general, various ways of connecting two rotational movements are known from text books of physics already, but especially when implemented according to preferable embodiments of the invention in a mammography apparatus containing at least two turnable arm parts, this new solution offers benefits that are described more precisely in the following, expressly in connection with the aforementioned mammography screening examinations.

In view of preferable embodiments of the invention, one noticeable special situation is where it is desired that one of the arm parts will turn into a certain angle with respect to the other, but this other maintains its position with respect to the support structure 21 of the apparatus. Such a movement will be achieved, in addition to, naturally, by using an actuator turning only one arm part, by driving the actuator turning the whole arm structure in one direction and the actuator turning one arm part at a corresponding angular velocity but in the opposite direction. Generally speaking, the said one arm part may be any of the arm parts of the arm structure, but according to the invention it is preferably the "second" (lower) arm part 22', which expressly in a mammography apparatus may be arranged to be smaller and lighter. Regarding many of the operations related to use of the imaging apparatus according to the invention such an action brings about more ease and speed, of which some examples in the following.

Figure 3A:
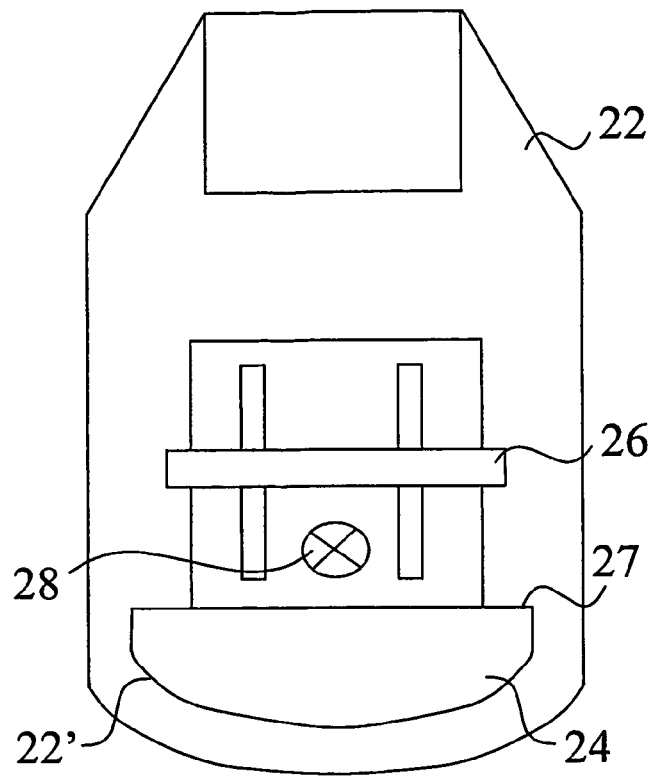
Figure 3B:
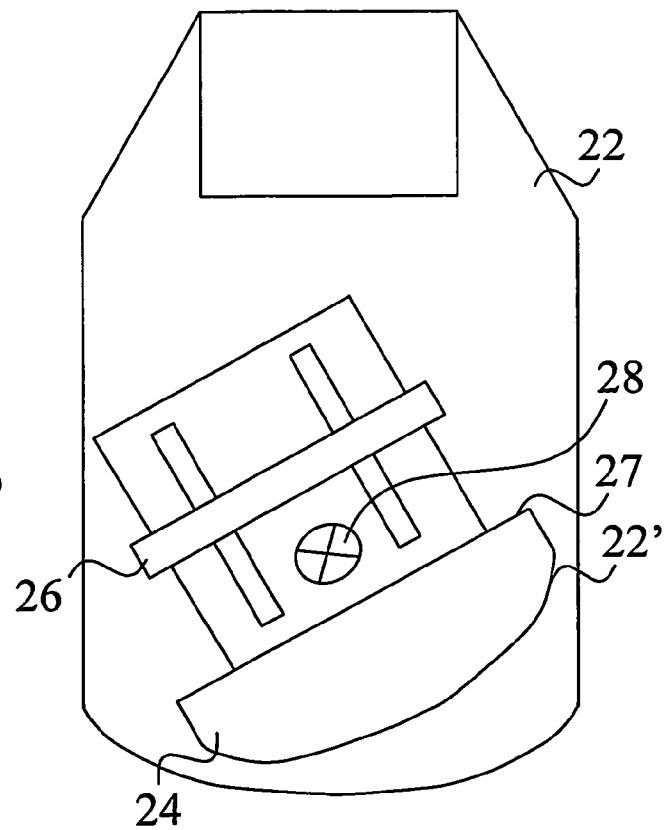
Figure 3C:
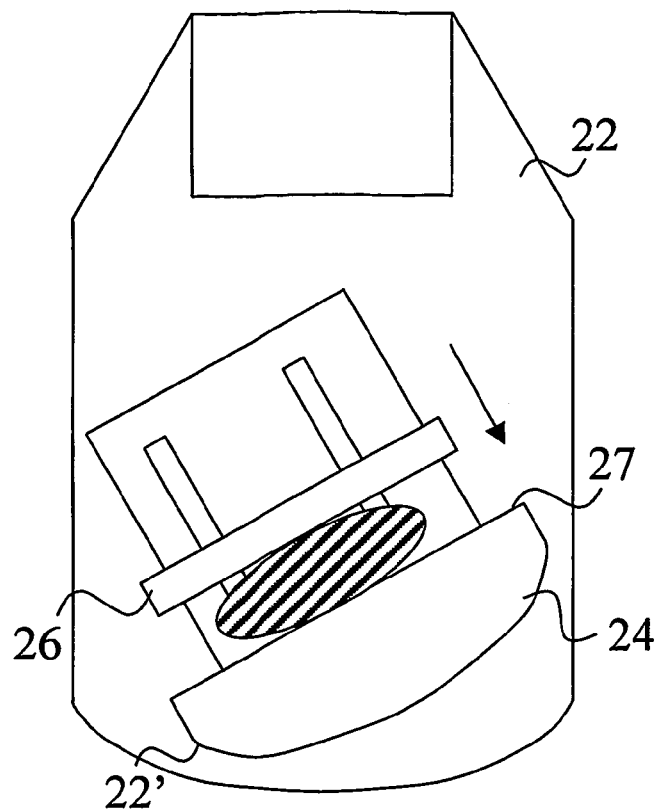
Figure 3D:
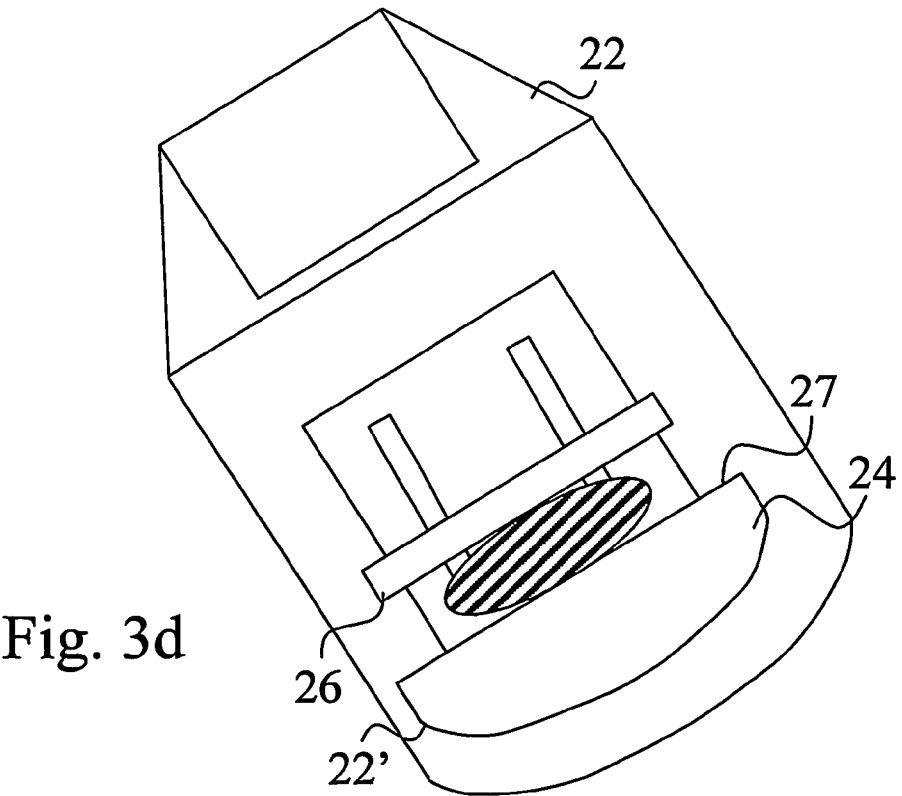

In FIGS. 3a-3d there is presented an operation sequence enabled by the structure of the apparatus according to the invention. FIG. 3a presents a situation where the first and the second arm parts 22, 22' are in their "basic position", i.e. orientated parallel with each other—in case a structure according to FIGS. 1 and 2 being in question, also parallel with the vertical body part 11, 21 of the apparatus not shown in FIGS. 3a-3d. Now, the invention enables use of the actuators M, M' of the arm parts 22, 22' in such a way that the second (lower) arm part 22' is driven to an angular position according to an oblique view (FIG. 3b) by using the actuator M' turning only this arm part in question, the object is emplaced and compressed into its imaging position between the compression paddles 26, 27 by driving the upper compression paddle 27 down (FIG. 3c), and for the last the apparatus is made ready for imaging by turning also the first (upper) arm part 22 to its oblique view position (FIG. 3d), i.e. in a construction according to FIG. 2 by driving the actuator M turning the whole arm structure in the same direction as the actuator M' turning only the said second arm part 22' was first driven, and simultaneously driving the actuator M' turning the said second arm part 22' at a corresponding angular velocity but in the opposite direction. This way the first arm part 22, which could hamper patient positioning, can be "kept out of the way" as long as positioning of the object has been completed, and the second arm part 22' be driven to its imaging position only after the positioning has been completed.

One of the special tailored views, which many of the modern mammography apparatuses enable, is a so-called PA (posterior-anterior) imaging, where the breast is imaged from underneath, i.e. where the radiation source is driven, typically, into an angle below the object to be imaged. Even in this kind of a case the invention may be utilized for keeping the radiation source concretely "out of the way", in which case the person assisting positioning does not have to reach over the arm structure. Now it is possible to proceed e.g. in such a way that, when starting e.g. from a vertical orientation according to FIG. 3a, first only the actuator M turning the whole arm structure will be driven until a desired oblique view angle has been reached, then both of the actuators will be operated at the same speed in different directions, whereby the second arm part 22' stays at its place and the first arm part 22 goes on e.g. until it reaches vertical orientation downwards, the object will be positioned as described in the previous example and further, by using the actuators as in the previous phase but in opposite directions, also the first arm part 22 will be driven into its place of its imaging station.

The invention thus offers not only possibilities for facilitating patient positioning in general, but also enables expressly a flexible emplacement of the arm parts for implementing this kind of an application. In many situations, by a construction according to the invention, relatively faster and more flexible way of bringing the arm parts into their desired new emplacement will be achieved as compared to e.g. a structure where there would be available a construction containing one actuator turning the arm structure as a whole and means for stopping movement of one arm part of the arm structure. As an example one may consider a situation where, after the previous imaging has been completed, the imaging apparatus is in an oblique view position and where it should be driven into a patient emplacement position of an imaging from vertical position (where the arm parts at their starting positions are orientated parallel, e.g. at an angle of 45 degrees with respect to vertical, and at their end position e.g. the upper arm part at an angle of 30 degrees with respect to vertical, and the lower one in vertical). In such a case, according to a construction as described, one would have to first drive the arm structure to vertical, lock the lower arm part (with respect to the support structure of the apparatus) and only then would it be possible to drive the upper arm part to its emplacement position at 30 degrees, but e.g. by the construction according to FIG. 2 as described above, the need for driving the upper arm part to vertical may be completely avoided as the actuator M turning both of the arm parts may simply be stopped already during "the first movement" at the position of 30 degrees, and continue by driving only the lower arm part 22' into vertical.

The invention enables, however, e.g. an even more flexible implementation of the operation as described above, too. By operating e.g. both of the actuators simultaneously in the same direction, for example during the "first movement" according to that example, the lower arm part 22', which will have to turn a larger angle, will move in the same direction at an angular velocity which is the sum of the angular velocities produced by individual actuators, whereby that longer-movement in question will be executed more quickly. Further, the rotating speed of e.g. the actuator M' turning only the lower arm part 22' may be arranged to be higher than that of the actuator M turning the whole arm structure, which in a situation as described above enables emplacement of the imaging means into their next desired position even quicker than before. Preferably, such a difference of speeds may be realized e.g. just in such a structure according to the preferable embodiment as described above where the traditional C-arm of a mammography apparatus, being made of one part, has been divided into two in such a way that the lower arm part 22', including image data receiving means, is remarkably lighter by its mass than the upper arm part 22 containing a heavy x-ray tube whereby, depending in which mutual relation the pivot angles of the arm parts 22, 22' that are needed at a time are, and on the angular velocities used for the separate arm parts, it is possible e.g. in the example as described above to realize the whole movement as an even one by a proper choice of ratio of the angular velocities, i.e. in such a way that the movements begin and end simultaneously as both of the arm parts reach their desired emplacement at the same time. Benefit of one even movement is not only "stylistic matters" but, among others, the fact that in this way the masses to be rotated need not to be accelerated and slowed down/stopped more than once as a consequence of change of emplacement. Certainly, in case adjustable turning speed is arranged e.g. expressly to the lighter lower arm part 22', the movements of the arm parts may, of course and if so desired, be implemented by proper arrangements in such a way that despite of a possibly greater pivot angle, the lower arm part 22' will reach its desired emplacement faster than the upper one.

The imaging apparatus with its control arrangements and user interface may be realized e.g. in such a way that the next desired emplacement of the arms will be fed from the user interface. The imaging apparatus may be realized in many ways known to a man skilled in the art such that the control arrangement will "know" at a time in which position the arm parts are located, so that after having received a transfer command it can e.g. calculate the angular velocities/ratio of the angular velocities by which the arm parts are to be driven in order that they would reach their desired emplacements at the same time. There may also be built into the control arrangement various ready-to-use driving sequences corresponding to the ways of imaging frequently repeating and/or arranged a possibility for the user to create by oneself sequences to meet frequently repeating imaging needs of one's own. E.g. a command given from the user interface to move to an imaging position A may be arranged to correspond a concrete operation sequence where the arm parts first move automatically to a patient positioning emplacement corresponding the imaging emplacement in question, and to the actual imaging emplacement only after the control arrangement has received a signal "positioning ready". The control arrangement of the imaging apparatus altogether may thus be arranged to contain the necessary means and control routines for driving the arm parts from a first position into a second one, whereby the control routine in question may contain a routine for driving at least two arm parts into at least one emplacement where their mutual orientation has been essentially deviated from parallel one, a routine with help of which desired control sequences for the arm parts may be construed into the control arrangement, and to contain means for following and/or identifying the mutual orientation of the arm parts and/or their orientation with respect to the support structures of the apparatus.

In the above there has been described a preferable embodiment of the invention where movement of the second arm part 22' with respect to the first arm part 22 is realized with help of an independent actuator M' arranged for the second arm part 22'. By laying aside some objects of the invention, especially concerning the goal of a structure that would be mechanically relatively simple and e.g. possibility for an easy and flexible adjustment of movements via programmatically usable actuators, like step motors, the actuator M' of the second arm part 22' may certainly be replaced e.g. by such a gear structure through which the corresponding movements of the arm parts with respect to each other, and to the support structures of the mammography apparatus, may be reached as by a solution according to FIG. 2 by using only the actuator M of the first arm part 22. Essentially the preferable embodiment of the invention includes, however, at least the first and the second arm part, which are arranged turnable en block with respect to the support structures of the apparatus on one hand and, on the other hand, at least one of the arm parts has been arranged with means for changing mutual orientation of at least two of the arm parts, whereby the first of the said at least two arm parts arranged turnable with respect to each other has been arranged to include a radiation source, and the second to include means for receiving image data. Especially preferable is to choose the lighter lower arm part to be the arm part that will be turned independently and the actuator turning it integrated thereto, the pivot axis of the arm parts arranged to coincide and essentially also onto the level whereto the tissue to be imaged is positioned in contact imaging—onto the lower compression paddle which unites with or forms the lower shelf structure.

The invention does not exclude the alternative that the arm structure includes more than two arm parts. Further, one may consider that the pivot axes of the turnable arm parts do not coincide, or that a construction consisting of more than two arm parts will be arranged to include more than one pivot axis, which enable changing the mutual orientation of the arm parts. Most preferably the objects of the invention will be reached, though, especially by the embodiment that has been described in more detail above.

The invention claimed is:

1. Mammography imaging apparatus, which contains either an essentially vertically standing body part or a support structure (21) attachable to a wall or a ceiling, and an arm structure in connection with it, being turnable with respect to a horizontal rotating axis (28), a radiation source (23) on one hand and image data receiving means (25) on the other hand being placed at essentially opposite ends of the arm structure, which arm structure includes at least two arm parts (22), (22') orientating essentially parallel and means for changing the mutual orientation of at least a first and a second of the said at least two arm parts, wherein the apparatus includes first means (M) for turning the arm structure, including said at least two arm parts, as a whole around a horizontal axis and that to the said second arm part (22') is arranged second means (M') for turning said second arm part with respect to said first arm part.

2. Imaging apparatus according to claim 1, wherein said first arm part (22) contains said radiation source (23) of the imaging apparatus and the said second arm part (22') contains said means for receiving image data (25).

3. Imaging apparatus according to claim 2, wherein said second arm part (22') contains a lower shelf structure (24) having at least an essentially planar upper surface, essentially in direction of its pivot axis.

4. Imaging apparatus according to claim 3, wherein the pivot axis of the said second arm part (22') is arranged at a distance on the order of centimeters, from the upper surface of the lower shelf structure (24) belonging to it.

5. Imaging apparatus according to claim 4 wherein the pivot axis of said second arm part (22') is arranged at a distance in the range of between about 2 to 3 cm from the upper surface of the lower shelf structure (24) belonging to it.

6. Imaging apparatus according to claim 1, wherein said first means comprises a first actuator coupled to said first arm part and said second means comprises a second actuator (M') coupled to said second arm part (22').

7. Imaging apparatus according to claim 1, wherein the radiation source has a focus and the dimensions of the said arm structure are arranged such that when the arm parts (22), (22') are orientated essentially parallel, the distance from the focus of the radiation source (23) to the image data receiving means (25) is in the order of magnitude of between about 60 to 80 cm.

8. Imaging apparatus according to claim 1, wherein the pivot axis of the said second arm part (22') is arranged to coincide with the pivot axis of the said first arm part (22).

9. Imaging apparatus according to claim 1, wherein said second arm part (22') contains a compression structure 26, 27, which positions the tissue to be imaged into the imaging area.

10. Imaging apparatus according to claim 9, wherein said compression structure contains an upper compression plate (26) and a lower compression plate (27), which lower compression plate (27) comprises only the lower shelf structure (24) of the said second arm part (22'), which contains the image data receiving means (25).

11. Imaging apparatus according to claim 1, wherein the imaging apparatus includes a control arrangement via which the said first and second means (M), (M') are arranged to be programmatically drivable.

12. Imaging apparatus according to claim 1, wherein said means (M,M') are arranged to enable turning the arm parts (22, 22') at different angular velocities in the same direction with respect to each other.

13. Imaging apparatus according to claim 1, wherein said means (M, NI') are arranged to enable turning the arm parts (22, 22') such that while the first arm part turns in one direction, the second arm turns in the opposite direction.

14. Method for turning an arm structure of a mammography imaging apparatus, which arm structure contains either a vertical base part or support structure attachable to a wall or a ceiling, and a structure in connection with it that is turnable with respect to a horizontal rotating axis, which structure has on one hand a radiation source and on the other hand image data receiving means located essentially at the opposite ends of it, which arm structure includes at least two arm parts orientating essentially parallel, and means for changing mutual orientation of at least a first and a second of the said at least two arm parts, wherein while the said first arm part is rotated around a horizontal axis, the said second arm part is rotated either in the same direction at a different angular velocity as said first arm, or in a direction opposite to the direction of rotation of the first arm.

15. Method according to claim 14, wherein said first arm part is rotated by the same actuator by which the arm structure as a whole is capable of being rotated.

16. Method according to claim 14, wherein said second arm part is rotated by an actuator integrated to the said arm part.

17. Method according to claim 14, wherein one moves from a first position of the arm structure, where the said at least first and second arm parts are orientated essentially parallel with respect to each other, to another corresponding position, such as from a previous imaging position to a subsequent imaging position, according to a motion-sequence which contains such an intermediate phase where the said first and second arm parts are essentially in some other orientation than parallel.

18. Method according to claim 17, wherein said sequence contains at least one phase where the said second arm part is rotated in a different direction but at the same angular velocity as the said first arm part.

19. Control arrangement of a mammography imaging apparatus, which contains means and control routines for realizing actions according to the method of claim 14.

20. Control arrangement according to claim 19, wherein it contains at least one control routine for driving the arm parts from a first position to a second one.

21. Control arrangement according to claim 20, wherein said control routine contains driving of the arm parts into at least one position where the mutual orientation of at least two arm parts has been essentially deviated from parallel orientation.

22. Control arrangement according to claim 19, wherein said program routines include routines with help of which desired control sequences for the arm parts may be created into the control arrangement.

23. Control arrangement according to claim 19, wherein it contains means for following and/or recognizing the mutual orientation of the arm parts, and/or their orientation with respect to support structures of the apparatus.

* * * * *